(12) United States Patent
Pizza

(10) Patent No.: US 9,649,296 B1
(45) Date of Patent: *May 16, 2017

(54) HEAT STERILIZEABLE, PREMIXED, READY TO USE DEXMEDETOMIDINE SOLUTION PACKAGED IN A FLEXIBLE PLASTIC CONTAINER

(71) Applicant: SLYPHARMA, LLC, Palm Beach, FL (US)

(72) Inventor: Joseph M. Pizza, Palm Beach, FL (US)

(73) Assignee: SLYPHARMA, LLC., Palm Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/185,519

(22) Filed: Jun. 17, 2016

Related U.S. Application Data

(63) Continuation of application No. 15/133,922, filed on Apr. 20, 2016.

(51) Int. Cl.
*A61K 31/4164* (2006.01)
*A61K 31/4174* (2006.01)
*A61K 47/26* (2006.01)
*A61J 1/14* (2006.01)

(52) U.S. Cl.
CPC ......... *A61K 31/4164* (2013.01); *A61J 1/1468* (2015.05); *A61K 47/26* (2013.01)

(58) Field of Classification Search
CPC .................. A61K 31/4174; A61K 31/4164
USPC ....................................................... 514/396
See application file for complete search history.

(56) References Cited

U.S. PATENT DOCUMENTS

| | | | |
|---|---|---|---|
| 4,544,664 A | 10/1985 | Karjalainen et al. | |
| 4,670,455 A | 6/1987 | Virtanen et al. | |
| 4,910,214 A | 3/1990 | Karjalainen et al. | |
| 5,091,402 A | 2/1992 | Kalso et al. | |
| 5,124,157 A | 6/1992 | Colley et al. | |
| 5,139,831 A * | 8/1992 | Mueller | B32B 27/08 264/211 |
| 5,217,718 A | 6/1993 | Colley et al. | |
| 5,304,569 A | 4/1994 | Lammintausta et al. | |
| 5,344,840 A | 9/1994 | Maze et al. | |
| 5,712,301 A | 1/1998 | Jaatinen et al. | |
| 6,716,867 B1 | 4/2004 | Aantaa et al. | |
| 8,242,158 B1 * | 8/2012 | Roychowdhury | A61K 31/4174 514/396 |
| 2010/0094219 A1 | 4/2010 | Kriesel et al. | |
| 2014/0155446 A1 | 6/2014 | Roychowdhury et al. | |
| 2015/0098980 A1 | 4/2015 | Pongpeerapat et al. | |

FOREIGN PATENT DOCUMENTS

WO 2011/004390 A2 1/2011

OTHER PUBLICATIONS

VisIV information from https://www.hospira.com/en/products_and_services/drugs/visiv.*
International Search Report and Written Opinion dated Sep. 19, 2016 issued in corresponding application PCT/US2016/039776.

* cited by examiner

*Primary Examiner* — San-Ming Hui

(74) *Attorney, Agent, or Firm* — Oblon, McClelland, Maier & Neustadt, L.L.P.

(57) ABSTRACT

The presently disclosed subject matter relates to pharmaceutical compositions comprising dexmedetomidine or a pharmaceutically acceptable salt thereof wherein the composition is formulated as a liquid for parenteral administration to a subject, and wherein the composition is disposed in a flexible plastic container as a ready to use premixed solution.

18 Claims, No Drawings

HEAT STERILIZEABLE, PREMIXED, READY TO USE DEXMEDETOMIDINE SOLUTION PACKAGED IN A FLEXIBLE PLASTIC CONTAINER

FIELD OF THE INVENTION

The present invention relates to patient-ready, premixed formulations of dexmedetomidine, or a pharmaceutically acceptable salt thereof, used in perioperative care of a patient or for sedation and other uses.

BACKGROUND OF THE INVENTION

Racemic 4-[1-(2,3-dimethylphenyl)ethyl]-1H-imidazole, which is known under the name medetomidine, is a selective and potent $\alpha_2$-adrenoceptor agonist. Medetomidine is used as an antihypertensive agent and as a sedative-analgesic agent. This compound also possesses anxiolytic effects and can therefore be used in the treatment of general anxiety, panic disorder and various types of withdrawal symptoms.

The d-enantiomer of medetomidine, the generic name of which is dexmedetomidine, is described in U.S. Pat. No. 4,910,214 as an $\alpha_2$-adrenoceptor agonist for general sedation/analgesia and the treatment of hypertension or anxiety. U.S. Pat. Nos. 5,344,840 and 5,091,402 discuss dexmedetomidine use in perioperative and epidural applications, respectively. When used in perioperative care, dexmedetomidine can reduce the amount of anesthetic necessary to anesthetize a patient. Additionally, U.S. Pat. No. 5,304,569 discusses using dexmedetomidine in treating glaucoma, and U.S. Pat. No. 5,712,301 discusses using dexmedetomidine for preventing neurodegeneration caused by ethanol consumption. U.S. Pat. No. 6,716,867 discloses methods of sedating a patient in an intensive care unit by administering dexmedetomidine, or a pharmaceutically acceptable salt thereof, to the patient.

Dexmedetomidine is administered to a patient in a variety of ways. U.S. Pat. Nos. 4,544,664 and 4,910,214 disclose the administration of dexmedetomidine via parenteral, intravenous, and oral routes. U.S. Pat. No. 4,670,455 describes intramuscular and intravenous administration, while U.S. Pat. Nos. 5,124,157 and 5,217,718 describe a method and device for administering dexmedetomidine through the skin. Additionally, U.S. Pat. No. 5,712,301 states that dexmedetomidine can be administered transmucosally.

Premixed dexmedetomidine solutions are described in U.S. Pat. No. 8,242,158. The premixed dexmedetomidine solutions are packaged in glass vials because of the tendency of dexmedetomidine to be either adsorbed or absorbed by plastic materials. The patent discloses that up to 20% of the dexmedetomidine is lost through adsorption. The patent reports the cause of potency loss in PVC bags and CR3 elastomer copolyester ether bags (Hospira, Inc., Lake Forest, Ill.) during autoclaving was investigated. Related substances testing on autoclaved premixed dexmedetomidine composition filled in PVC and CR3 elastomer copolyester ether bags (Hospira, Inc., Lake Forest, Ill.) revealed that potency drop did not occur due to degradation, because the total percent of impurities was much less than 20%. Loss of potency may be due to either adsorption (restricted to the surface of the bag) and/or absorption (not restricted to the surface) of the drug into the bags. To confirm the absorption/adsorption phenomena, the CR3 elastomer copolyester ether bags (Hospira, Inc., Lake Forest, Ill.) and PVC bags that showed 20% potency loss were emptied and rinsed with MeOH and the rinse solvent tested for dexmedetomidine. Nearly all the drug was recovered from CR3 elastomer copolyester ether bags (Hospira, Inc., Lake Forest, Ill.)—indicating adsorption and only 1% of the drug was recovered from PVC bags— indicating absorption, since drug dissolves in DEHP. The loss of dexmedetomidine can be reduced by including a buffer system in the formulation but even with a buffer drug loss on the order of 10% is experienced. The patent also reported that Vis-IV™ bags (Hospira, Inc., Lake Forrest, Ill.) had higher impurity levels than either the PVC and CR3 elastomer copolyester bags. All of the plastic containers contained more impurities than the glass ampules, vials and syringes tested.

Flexible plastic containers for drugs are preferred because of ease of storage and the inherent non-breakable properties of the flexible plastic containers. Thus, a need continues to exist for a ready-to-use dexmedetomidine solution packaged in flexible plastic containers.

SUMMARY OF THE INVENTION

The present inventors have solved the problem of storing premixed dexmedetomidine solutions in plastic containers by using one or more sugars as the tonicity adjusting agent in the dexmedetomidine formulation.

In a further embodiment the plastic container is a flexible container.

In yet another embodiment the flexible plastic container comprises a laminated bag having an inner layer comprising a styrene-ethylene-butylene-styrene (SEBS) copolymer and an ethylene-propylene copolymer.

In still a further embodiment the dexmedetomidine solution has been heat sterilized in the flexible plastic container.

In a still further embodiment, the flexible plastic container is a bag.

It is yet another embodiment that the Dexmedetomidine solution is isotonic.

It is a still further embodiment that the tonicity adjusting agent is a sugar.

The premixed formulation of this invention can be used in the same manner and for the indications as dexmedetomidine has been used previously.

DETAILED DESCRIPTION

According to the present invention, the term "dexmedetomidine" as used herein refers to a substantially pure, optically active dextrorotary stereoisomer of medetomidine, as the free base or pharmaceutically acceptable salt. In one, non-limiting embodiment, dexmedetomidine has the formula (S)-4-[1-(2,3-dimethylphenyl)ethyl]-3H-imidazole. Pharmaceutically acceptable salt of dexmedetomidine include inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. Preferably, the dexmedetomidine salt is dexmedetomidine HCl.

The terms "premix" or "premixture" as used herein refers to a pharmaceutical formulation that does not require reconstitution or dilution prior to administration to a patient. For example, in contrast to non-premixed formulations of dexmedetomidine, the premixed compositions provided herein are suitable for administration to a patient without dilution.

In certain embodiments, the compositions of the present invention can be formulated as "ready to use" compositions that refer to premixed compositions suitable for administration to a patient without dilution. For example, in certain embodiments, the compositions of the present invention are "ready to use" upon removing the compositions from a sealed container or vessel.

In certain embodiments, the compositions of the present invention may be formulated as a "single use dosage," which refers to a premixed composition that is disposed within a sealed plastic container or vessel as a one dose per container or vessel formulation.

The compounds and compositions of the invention may be formulated as pharmaceutical compositions by admixture with a pharmaceutically acceptable carrier or excipient. In certain non-limiting embodiments, the compounds or compositions are provided in a therapeutically effective amount to an animal, such as a mammal, preferably a human, in need of treatment therewith for inducing a sedative, anxiolytic, analgesic, or anesthetic effect.

In certain non-limiting embodiments, dexmedetomidine is formulated as a composition, wherein the dexmedetomidine is the only therapeutically active ingredient present in the composition. In another non-limiting embodiment, dexmedetomidine is formulated as a composition, wherein the dexmedetomidine is formulated in combination with at least one or more other therapeutically active ingredient. The formulation is preferably suitable for parenteral administration, including, but not limited to, intravenous, subcutaneous, intramuscular and intraperitoneal administration; however, formulations suitable for other routes of administration such as oral, intranasal, mucosal or transdermal are also contemplated.

The pharmaceutical formulations suitable for injectable use, such as, for example, intravenous, subcutaneous, intramuscular and intraperitoneal administration, include sterile aqueous solutions or dispersions and sterile powders for the extemporaneous preparation of sterile injectable solutions or dispersion. In all cases, the form can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, saline, ethanol, polyol (for example, glycerol, propylene glycol, and polyethylene glycol, and the like), suitable mixtures thereof, and oils. The proper fluidity may be maintained, for example, by the use of a coating such as lecithin, by the maintenance of the required particle size in the case of dispersion and by the use of surfactants. The preventions of the action of microorganisms may be achieved by various antibacterial and antifungal agents, for example, parabens, chlorobutanol, phenol, benzyl alcohol, sorbic acid, and the like.

It is preferable to include sugars as isotonic agents such as dextrose, mannitol, glycerol, and sucrose as other conventional isotonic agents including ionic salts such as sodium chloride increase substantially the adsorption and/or absorption of the Dexmedetomidine by the plastic container.

Prolonged absorption of the injectable compositions by the patient may be brought about by the use in the compositions of agents delaying absorption, for example, aluminum monosterate and gelatin. Sterile injectable solutions may be prepared by incorporating the dexmedetomidine in the required amounts in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above.

Preferably the formulation may contain an excipient. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA; liposomes; polyvinylpyrollidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. As used herein, the term "stabilizer" refers to a compound optionally used in the pharmaceutical compositions of the present invention in order to avoid the need for sulphite salts and increase storage life. Non-limiting examples of stabilizers include antioxidants. Buffer systems for use with the formulations include citrate; acetate; bicarbonate; and phosphate buffers. In selecting the excipients, it is necessary to test the formulation for adsorption or absorption of the dexmedetomidine by the plastic container.

The formulation also may contain a non-ionic detergent. Preferred non-ionic detergents include Polysorbate 20, Polysorbate 80, Triton X-100, Triton X-114, Nonidet P-40, Octyl .alpha.-glucoside, Octyl .beta.-glucoside, Brij 35, Pluronic, and Tween 20.

The parenteral formulations of the present invention may be sterilized. Non-limiting examples of sterilization techniques include filtration through a bacterial-retaining filter, terminal sterilization, incorporation of sterilizing agents, irradiation, and heating.

In certain non-limiting embodiments, the premixed dexmedetomidine composition comprises dexmedetomidine, or a pharmaceutically acceptable salt thereof, at a concentration of between about 0.005 µg/mL and about 100 µg/mL, or between about 0.005 µg/mL and about 50 µg/mL, or between about 0.005 µg/mL and about 25 µg/mL, or between about 0.005 µg/mL and about 15 µg/mL, or between about 0.005 µg/mL and about 10 µg/mL, or between about 0.005 µg/mL and about 7 µg/mL, or between about 0.005 µg/mL and about 5 µg/mL, or between about 0.005 µg/mL and about 4 µg/mL, or between about 0.005 µg/mL and about 3 µg/mL, or between about 0.005 µg/mL and about 2 µg/mL, or between about 0.005 µg/mL and about 1 µg/mL, or between about 0.005 µg/mL and about 0.5 µg/mL, or between about 0.005 µg/mL and about 0.05 µg/mL.

In certain non-limiting embodiments, the premixed dexmedetomidine composition comprises dexmedetomidine, or a pharmaceutically acceptable salt thereof, at a concentration of between about 3.5 µg/mL and about 4.5 µg/mL, or between about 3 µg/mL and about 5 µg/mL, or between about 2.5 µg/mL and about 5.5 µg/mL, or between about 2 µg/mL and about 6 µg/mL, or between about 1.5 µg/mL and about 6.5 µg/mL, or between about 1 µg/mL and about 7 µg/mL, or between about 0.5 µg/mL and about 10 µg/mL.

In certain non-limiting embodiments, the premixed dexmedetomidine composition comprises dexmedetomidine at a concentration of about 0.5 µg/mL, or about 1 µg/mL, or about 1.5 µg/mL, or about 2 µg/mL, or about 2.5 µg/mL, or about 3 µg/mL, or about 3.5 µg/mL, or about 4 µg/mL, or about 4.5 µg/mL, or about 5 µg/mL, or about 5.5 µg/mL, or about 6 µg/mL, or about 6.5 µg/mL, or about 7 µg/mL, or about 7.5 µg/mL, or about 8 µg/mL, or about 8.5 µg/mL, or about 9 µg/mL, or about 9.5 µg/mL, or about 10 µg/mL, or about 10.5 µg/mL, or about 11 µg/mL, or about 11.5 µg/mL, or about 12 µg/mL, or about 12.5 µg/mL, or about 13 µg/mL, or about 13.5 µg/mL, or about 14 µg/mL, or about 14.5 µg/mL, or about 15 µg/mL, or about 15.5 µg/mL, or about 16 µg/mL, or about 16.5 µg/mL, or about 17 µg/mL, or about 17.5 µg/mL, or about 18 µg/mL, or about 18.5 µg/mL or about 19 µg/mL, or about 19.5 µg/mL, or about 20 µg/mL.

The premixed dexmedetomidine composition preferably comprises dexmedetomidine at a concentration of about 4 µg/mL.

The premixed dexmedetomidine composition is formulated at a pH of between about 1 and about 10, or between about 1 and about 8, or between about 1 and about 6, or between about 1 and about 4, or between about 1 and about 2. Preferably, the premixed dexmedetomidine composition is formulated at a pH of between about 2 and about 10, or between about 4 and about 8, or between about 4 and about 7. More preferably, the premixed dexmedetomidine composition is formulated at a pH of between about 4.0 and about 6.0.

In other non-limiting embodiments, the premixed dexmedetomidine composition comprises dexmedetomidine mixed or dissolved in a solution comprising a suitable sugar as the tonicity adjusting agent. The particular sugar tonicity adjusting agent is not critical. The amount of the tonicity adjusting agent is not critical but generally a sufficient amount is used to achieve an osmolality of between about 260 and 330 milliosmoles per kilogram of water.

The preferred tonicity agent is dextrose. The amount of dextrose or other tonicity adjusting sugar used is determined by the osmolality of solution prior to adding the tonicity adjusting sugar. It is preferred that sufficient sugar be added to achieve an osmolality of between about 260 and 330 milliosmoles per kilogram of water when the drug is administered by intravenous means although higher and lower osmolality can be used if desired.

In certain embodiments, the weight percent of the sugar solution is a percent weight/weight of the premix composition. In certain embodiments, the weight percent of the sugar solution is a percent weight/volume of the premix composition.

In certain non-limiting embodiments, the premixed dexmedetomidine composition of the present invention comprises dexmedetomidine, or a pharmaceutically acceptable salt thereof, at a concentration of between about 0.05 µg/mL and about 15 µg/mL, and a sugar at a concentration to provide a solution which is approximately isotonic.

In other non-limiting embodiments, the premixed dexmedetomidine composition of the present invention comprises dexmedetomidine, or a pharmaceutically acceptable salt thereof, at a concentration of about 4 µg/mL and dextrose at a concentration of 5 weight percent.

A 5% dextrose solution may be formulated by mixing 5 grams of dextrose in 1000 ml of water. In certain embodiments, the premix compositions of the present invention are formulated by adding 0.118 g dexmedetomidine HCl plus 5 grams dextrose into the same 1000 mL of water. The solution can then be mixed with additional 5% dextrose solution to achieve a desired concentration of dexmedetomidine, for example, 4 µg/mL. When a buffer is used, the amount of dextrose may be adjusted to account for the presence of the buffer since the presence of a buffer will impact the solution's osmolality.

The premixed dexmedetomidine solution may contain buffers such as citrate; acetate; bicarbonate; and phosphate buffers. However, the use of buffers is not preferred as it desired to keep the formulation as simple as possible. If a buffer is used, the buffer chosen should be selected so as to not increase the amount of Dexmedetomidine lost to adsorption or adsorbtion by the plastic container.

The flexible plastic container must be one which does not adsorb dexmedetomidine. It must also be able to undergo heat sterilization in moist steam without contaminating the dexmedetomidine solution. Suitable flexible plastic containers are those made of copolymerized ethylene and vinyl acetate. Preferably the bag is laminated with the inner most layer comprising copolymerized ethylene and vinyl acetate. More preferably the bag comprises from 3 to 7 layers. These materials are commercially available under the tradename Nexcel® by Sealed Air. The volume of the bag is dependent on the volume of premixed formula. The volume of premixed formula can be from 10 ml to 1000 ml, preferable 50 ml and 100 ml based on current dexmedetomidine dosing. Larger or smaller volumes can be used depending on dosing requirements. CR3 elastomer copolyester ether bags may also be used for formulations to be sterilized in moist steam provided but are not preferred.

If the dexmedetomidine formulation is aseptically sterilized in addition to the bags having at least the inner most layer comprising a styrene-ethylene-butylene-styrene (SEBS) and an ethylene-propylene copolymer, bags made of CR3 elastomer copolyester ether bags, or bags made of a polyolefin (Hospira VISIV bags) may be used. PVC may be successfully used for the aseptically sterilized dexmedetomidine formulation provided specific bag does not absorb the dexmedetomidine. Dexmedetomidine has been reported in U.S. Pat. No. 8,242,158 as being soluble in DEHP used as a plasticizer in many PVC bags. Accordingly the bag should be substantially free of DEHP. Substantially free of DEHP means that the amount of DEHP present is insufficient to appreciably impact the amount of dexmedetomidine retained in the solution upon storage stability testing. That is, the amount of dexmedetomidine remains at or above 90% of the initial level.

In an embodiment of the present invention, provided are a flexible plastic container with modified ports and closure system suitable for storing dexmedetomidine formulations of the present invention which is subjected to typically product sterilization by steam sterilization (e.g., autoclaving, 121° C. for a about 15 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition to plastic bags, CZ resin containers, polypropylene and similar resins can be used as rigid containers and syringes.

The ports and the closure system preferably uses commerciality available polymers, elastomers etc. In an exemplary embodiment of the present invention, the administrative and additive ports can be made off external coextruded layer consists of synthetic thermoplastic rubber (Raumedic SRT320) ranging from about 20 to 30% based on an elastomer modified polypropylene. While the internal coextruded layer (PE770) of not more that 50% in composition consists of ethylene vinyl acetate without any further additives (EVA). The tubing ports can be made of two-layer materials, which can withstand both terminal sterilization and co-solvent matrix. Furthermore, the twist-off compositions can be made of polyproplene Granuflex® 4489 between 70-80% and Granuflex®4371 15-20%. Alternatively the port tube may be a bilayer tube comprising an outer layer of polypropylene and an inner layer of EVA and the twist off made of LDPE and PP. However, other polymers stable, low leachables, and without physical deformation during heat sterilization may also be used for the ports and closure assemblies.

Commercially available flexible plastic containers (bags) such as Excel® (Braun Company) comprising a three-layered ethylene-polypropylene bag having polyester elastomer outer layer, Visiv® (Hospira), Nexcel® (Sealed Air), Intervia® (Baxter) preferably with a non-DEHP fluid path, Technoflex polyolefin bags, etc., for pharmaceutical formulation or medical liquids are assembled of different plastic materials of different properties, thermal resistance and functionalities. They are typically designed and tested mostly for aqueous formulations admixtures, premixed or ready-to-use pharmaceutical products. Still the combination of the co-solvents and drug composition subjected to further heat sterilization can adversely effect, plastic materials, sealing integrity and the solutions contained therein unless they are maintained at certain conditions. Thus, the plastic container should be checked after sterization for integrity before using it for the formulation. In addition, the formulation after sterization should be analyzed for the presence of substances leached from the container as a result of the sterilization cycle.

In another alternative embodiment, provided are a flexible plastic container with modified ports and closure system suitable for storing dexmedetomidine formulations of the present invention which is subjected to typically product sterilization by steam sterilization (e.g., autoclaving, 121° C. for a about 15 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc.

Sterilization may be accomplished by any of the conventional methods including aspectic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A preferred formulation comprises 4 to 5 microgram per milliliter Dexmedetomidine, about 45 to 55 milligrams per milliliter of dextrose and sufficient water to provide a 1 milliliter solution in flexible plastic bag. The formulation is terminally sterilized from about 15 to 25 minutes at 120 to 130 degrees C. A more preferred formulation comprises about 4.7 micrograms Dexmedetomidine, about 50 milligrams dextrose and water sufficient to provide a 1 milliliter volume solution in flexible plastic bags. The formulation is terminally sterilized at about 121 degrees C. for about 15 minutes.

Having generally described this invention, a further understanding can be obtained by reference to certain specific examples, which are provided herein for purposes of illustration only, and are not intended to be limiting unless otherwise specified.

Example 1

A composition was prepared containing 4.0 μg Dexmedetomidine and 50 mg dextrose to adjust tonicity with sufficient water to bring the total volume to 1 mL. The formulation was filled into Nexcel bags with two ports, a polypropylene port and a rubber port, autoclaved and with some bags stored at 25° C.±2° C./40% RH±5% RH and others at 40° C.±2° C./15% RH±5% RH for accelerated stability testing. The results are shown in Tables 1 and 2.

TABLE 1

Accelerated Storage Stability
40° C. ± 2° C./15% RH ±5% RH
DEXMEDETOMIDINE 200 MICROG/50 ML

| | Specification | 0 months | 1 month | 3 months | 6 months |
|---|---|---|---|---|---|
| Appearance of Solution | Colorless | Colorless | Colorless | Colorless | Colorless |
| Osmolality | 270-330 | 266 | 264 | 264 | 267 |
| Dexmedetomidine Assay | 90-110 | 99.8 | 94.2 | 94.6 | 95.5 |
| Unspecified Degradation Products (RRT 0.57) | ≤1.0 | 0.46 | 1.5 | 1.1 | 1.8 |

TABLE 2

Room Temperature Storage Stability
25° C. ± 2° C. /15% RH ±5% RH
DEXMEDETOMIDINE 200 MICROG/50 ML

| | Specification | 0 months | 3 months | 6 months |
|---|---|---|---|---|
| Appearance of Solution | Colorless | Colorless | Colorless | Colorless |
| Osmolality | 270-330 | 266 | 265 | 268 |
| Dexmedetomidine Assay | 90-110 | 99.8 | 92.6 | 100.6 |
| Unspecified Degradation Products (RRT 0.57) | ≤1.0 | 0.46 | 1.11 | 1.28 |

The accelerated test demonstrates that the solution will be stable at room temperature for about 24 months with little loss of Dexmedetomidine, the content remained within specifications. However an unidentified impurity was formed. This unidentified impurity was also formed at about the same rate in the samples stored at room temperature indicating it was not an artifact of the elevated temperature in the accelerated test. The source of this unidentified impurity was subsequently found to be the rubber injection port. This impurity can be avoided by changing the port to a polypropylene port or by simply using a single polypropylene port bag if necessary for regulatory approval. However, since the injection port was a standard one, the impurity is present in at least all bag formulations using this port.

The analyses of these tests demonstrates dexmedetomidine was not adsorbed or absorbed by the ethylene-vinyl acetate copolymer comprising inner-most bag layer. Thus, the present invention allows for the formulation of dexmedetomidine solutions in plastic containers a result considered to be impossible by the prior art. Thus, avoiding the use of glass containers previously used. The containers may either be rigid plastic containers or flexible containers, preferably bags because of ease of use and storage.

In similar tests only using a dexmedetomidine solution comprising 9 mg/mL sodium chloride retained only 93% of the dexmedetomidine after autoclaving in moist steam in the same Nexcel bag as in the foregoing tests. The presence of a buffer (28 g/mL sodium acetate and 320 mg/mL glacial acetic acid) with either dextrose or sucrose as the tonicity adjusting agent resulted in 99.4% and 99.0% retention of the dexmedetomidine after autoclaving in moist steam in the Nexcel bag. In contrast autoclaving in moist steam a dexmedetomidine formulation comprising 5.5 mg/mL of sodium chloride and 28 gram/mL sodium acetate and 320 mg/mL glacial acetic acid as a buffer retained only 90.1% of the dexmedetomidine after autoclaving.

Although the present invention has been described by reference to certain preferred embodiments, it should be understood that the preferred embodiments are merely illustrative of the principles of the present invention. Therefore, modifications and/or changes may be made by those skilled in the art without departing from the true spirit and scope of the invention as defined by the appended claims.

The invention claimed is:

1. A premixed, ready to use sterile dexmedetomidine solution comprising dexmedetomidine and dextrose packaged in a plastic container substantially free of DEHP.

2. The dexmedetomidine solution of claim 1 wherein the dexmedetomidine concentration is from about 0.5 to about 20 µg/ml.

3. The dexmedetomidine solution of claim 2 wherein the dexmedetomidine concentration is between about 4 to 6 µg/ml.

4. The dexmedetomidine solution of claim 2 wherein the solution consists essentially of dexmedetomidine, dextrose and water.

5. The dexmedetomidine solution of claim 4 wherein the plastic container is flexible.

6. The dexmedetomidine solution of claim 5 wherein the plastic container comprises an inner layer comprising a copolymer of ethylene and vinyl acetate.

7. The dexmedetomidine solution of claim 5 wherein the solution has been sterilized in moist steam.

8. The dexmedetomidine solution of claim 1 wherein the solution has been aseptically sterilized.

9. The dexmedetomidine solution of claim 3 wherein the dexmedetomidine concentration is about 4.0 µg/ml.

10. The dexmedetomidine solution of claim 8 wherein the dextrose concentration is about 50 mg/ml.

11. The dexmedetomidine solution of claim 1 wherein the plastic container is an ampule, vial or syringe.

12. The dexmedetomidine solution of claim 11 wherein the plastic container comprises an inner layer comprising a copolymer of an ethylene-propylene and copolymer and a Styrene-ethylene-butylene-styrene (SEBS).

13. A terminally sterilized Dexmedetomidine solution packaged in a plastic container having at least an inner layer comprising a copolymer of ethylene and vinyl acetate comprising about 4.7 micrograms/liter of Dexmedetomidine, 50 mg/l dextrose with remaining water and having a pH of from about 4.0 to 6.0.

14. The terminally sterilized Dexmedetomidine solution of claim 13 wherein said plastic container is flexible.

15. The terminally sterilized Dexmedetomidine solution of claim 14 wherein said plastic container is a bag.

16. The dexmedetomidine solution of claim 1 wherein the solution is isotonic, and the dexmedetomidine concentration is between about 4 to 7 µg/ml.

17. The dexmedetomidine solution of claim 1 wherein the dexmedetomidine is dexmedetomidine hydrochloride and the amount of dexmedetomidine hydrochloride is about 4.7 µg/ml.

18. A terminally sterilized dexmedetomidine hydrochloride solution packaged in a plastic container having at least an inner layer comprising a copolymer of Ethylene-propylene and a copolymer of styrene-ethylene-butylene-styrene (SEBS) comprising about 4.7 micrograms/liter of dexmedetomidine hydrochloride, 50 mg/l dextrose, with remaining water and having a pH of from about 4.0 to 6.0.

* * * * *